United States Patent [19]

Csapilla

[11] Patent Number: 5,414,094

[45] Date of Patent: May 9, 1995

[54] HIGH PURITY AND HIGH YIELD SYNTHESIS OF DIANHYDRIDES

[75] Inventor: Joseph Csapilla, Stamford, Conn.

[73] Assignee: Cytec Technology Corp., Wilmington, Del.

[21] Appl. No.: 471,297

[22] Filed: Jan. 26, 1990

[51] Int. Cl.$^6$ .......................................... C07D 307/06
[52] U.S. Cl. .................... 549/236; 549/234; 549/235; 549/240
[58] Field of Search ................ 549/234, 235, 236, 240

[56] References Cited

U.S. PATENT DOCUMENTS

| | | | |
|---|---|---|---|
| 3,410,876 | 11/1968 | Ralph | 549/234 |
| 3,769,304 | 10/1973 | Saluti | 549/236 |
| 4,614,808 | 9/1986 | Jürgen | 549/234 |

*Primary Examiner*—Emily Bernhardt
*Assistant Examiner*—Y. N. Gupta
*Attorney, Agent, or Firm*—Michael J. Kelly; Bart E. Lerman; Claire M. Schultz

[57] ABSTRACT

A process for making a dianhydride product, said process comprising reacting two moles of maleic anhydride and one mole of a vinyl benzene compound in a reaction mixture comprising about 1.5 to 2.0 moles of the vinyl benzene compound per mole of maleic anhydride at reaction temperature in the range from 105° to 125° C. for time to complete the reaction, adding a polar organic liquid to the reaction product mixture and refluxing the mixture, cooling the mixture following reflux and adding a hydrocarbon liquid to precipitate the product, separating the solid dianhydride product by filtration, washing the solids on the filter and drying the solids to make the finished dianhydride product.

6 Claims, No Drawings

HIGH PURITY AND HIGH YIELD SYNTHESIS OF DIANHYDRIDES

The invention relates to improvement in the process for making dianhydrides by reaction of maleic anhydride and a vinyl benzene compound. In a preferred process according to the invention, two moles of maleic anhydride is reacted with one mole of styrene to produce one mole of 3,4-dicarboxy-1,2,3,4-tetrahydro-1-naphtha-lenesuccinic dianhydride, sometimes called tetralin dianhydride.

U.S. Pat. No. 3,410,876 described the reaction of one mole of a vinyl benzene compound with two moles of maleic anhydride to produce a dianhydride of the kind produced by the present invention. Good yields (e.g. 90%) were obtained in examples using an excess of vinyl benzene in the reactant mixture to carry out the reaction, which was followed by filtration to separate precipitated product and recrystallization to purify the dianhydride product.

I have found that a dianhydride product of comparable purity can be obtained in comparable yields by a post reaction treatment of the reaction product before separation of the product by filtration from the reaction mixture, and without the need to recrystallize the product after filtration. An excess of the vinyl benzene reactant is used in the reaction mixture, in the range from about 1.5 to about 2.0 moles of vinyl benzene per mole of maleic anhydride to carry out the reaction. The reaction is carried out at about 105° to 125° C. and is usually completed in about 5 to 6 hours. On completion, a heavy slurry of the product dianhydride crystals in the excess styrene monomer is obtained. Before filtering this slurry, a quantity of acetonitrile is added in amount sufficient to solubilize most of the crystals at reflux temperature and the mixture is then heated to reflux for a few minutes. After reflux, the mixture is cooled to room temperature and a liquid hydrocarbon is added to precipitate more of the product. On filtration of the slurry and washing of the product solids on the filter, near 90% yield of white crystalline dianhydride product of good purity is obtained without need for recrystallization.

Instead of using acetonitrile as described I may use another polar organic liquid such as acetone, methyl ethyl ketone and the like. To precipitate the product, I may use a liquid hydrocarbon such as hexane, toluene, xylene or the like.

Other vinyl benzene reactants which may be used in my invention instead of styrene include ring substituted alkyl styrenes having 1-7 alkyl carbon atoms such as methyl styrenes, meta-divinylbenzene and the like. The dianhydride products obtained by using those reactants are described in more detail in U.S. Pat. No. 3,410,876.

A preferred mode for carrying out the invention is illustrated in more detail by reference to the following specific example.

EXAMPLE 1

In a heated, closed reactor equipped with a reflux condenser, 5 Kg. of maleic anhydride is melted at about 53° C. Thirteen grams of 2,5-di-t-butyl hydro-quinone is added as polymerization inhibitor. The reactor is purged with nitrogen and then purged with nitric oxide. While agitating the liquid, 8.76 liters of styrene is charged to the reactor. The molar ratio of maleic anhydride to styrene is 1 to 1.53. This reaction mixture is heated to reaction temperature in the range from 105°-125° C. and this temperature is maintained for about 5-6 hours as the reaction mixture is agitated under nitric oxide. About one hour into the reaction, the dianhydride product begins to crystallize. When the reaction is essentially complete, after 5 to 6 hours, two liters of acetonitrile is added to the liquid slurry as the heating is continued to maintain reflux at about 103° C. The mixture is refluxed for about 15 minutes and then the heating is stopped and the slurry begins to cool. Two liters of toluene is added slowly as the mixture is cooled to room temperature (10°-30° C.) and a slurry is formed of crystalline dianhydride product in the mixed liquids. This slurry is filtered at room temperature and the solids, which collect on the filter, are washed with two liters of toluene and 4000 ml hexane in succession and then dried to yield 6811 grams of crystalline, white product 3,4-dicarboxy-1,2,3,4-tetra-hydro-1-naphthalene succinic acid. The yield is 89%, melting point 200° C. Further purification by recrystallization is not necessary.

I claim:

1. A process for making a dianhydride product, said process comprising reacting two moles of maleic arthydride and one mole of a vinyl benzene compound in a reaction mixture comprising about 1.5 to 2.0 moles of the vinyl benzene compound per mole of maleic anhydride at reaction temperature in the range from 105° to 125° C. for time to complete the reaction, adding a polar organic liquid to the reaction product mixture and refluxing the mixture, cooling the mixture following reflux and adding a hydrocarbon liquid to precipitate the product, separating the solid dianhydride product by filtration, washing the solids on the filter and drying the solids to make the finished dianhydride product.

2. A process defined by claim 1 wherein the vinyl benzene is styrene.

3. A process defined by claim 2 wherein the hydrocarbon liquid is toluene.

4. A process defined by claim 1 wherein the polar organic liquid is acetonitrile.

5. A process defined by claim 2 wherein the polar organic liquid is acetonitrile.

6. A process defined by claim 3 wherein the polar organic solvent is acetonitrile.

* * * * *